United States Patent
Kohlstruk et al.

(10) Patent No.: US 7,557,242 B2
(45) Date of Patent: *Jul. 7, 2009

(54) MULTISTAGE CONTINUOUS PREPARATION OF CYCLOALIPHATIC DISOCYANATES

(75) Inventors: Stephan Kohlstruk, Duelmen (DE); Manfred Kreczinski, Herne (DE); Hans-Werner Michalczak, Herne (DE)

(73) Assignee: Degussa AG, Duesseldorf (DE)

( * ) Notice: Subject to any disclaimer, the term of this patent is extended or adjusted under 35 U.S.C. 154(b) by 455 days.

This patent is subject to a terminal disclaimer.

(21) Appl. No.: 11/100,603

(22) Filed: Apr. 7, 2005

(65) Prior Publication Data

US 2005/0250960 A1 Nov. 10, 2005

(30) Foreign Application Priority Data

May 7, 2004 (DE) .................. 10 2004 022 626

(51) Int. Cl.
C07C 251/00 (2006.01)
(52) U.S. Cl. .................. 560/344; 560/345; 560/338
(58) Field of Classification Search .............. 560/344, 560/345, 338
See application file for complete search history.

(56) References Cited

U.S. PATENT DOCUMENTS

| | | | |
|---|---|---|---|
| 2,692,275 A | 10/1954 | Bortnick et al. | |
| 3,919,279 A | 11/1975 | Rosenthal et al. | |
| 4,081,472 A | 3/1978 | Tsumura et al. | |
| 4,268,683 A | 5/1981 | Gurgiolo | |
| 4,386,033 A | 5/1983 | Koenig et al. | |
| 4,388,246 A | 6/1983 | Sundermann et al. | |
| 4,530,796 A | 7/1985 | Mattner et al. | |
| 4,596,678 A | 6/1986 | Merger et al. | |
| 4,596,679 A | 6/1986 | Hellbach et al. | |
| 4,692,550 A | 9/1987 | Engbert | |
| 4,713,476 A | 12/1987 | Merger et al. | |
| 4,851,565 A | 7/1989 | Merger et al. | |
| 5,087,739 A | 2/1992 | Bohmholdt et al. | |
| 5,360,931 A | 11/1994 | Bohmholdt et al. | |
| 5,386,053 A * | 1/1995 | Otterbach et al. | ............ 560/344 |
| 5,453,536 A | 9/1995 | Dai et al. | |
| 5,502,244 A | 3/1996 | Okawa et al. | |
| 5,616,784 A | 4/1997 | Schwarz et al. | |
| 5,646,328 A | 7/1997 | Deibele et al. | |
| 5,744,633 A | 4/1998 | Wilmes et al. | |
| 5,962,728 A | 10/1999 | Mason et al. | |
| 6,204,409 B1 | 3/2001 | Aso et al. | |
| 2005/0043561 A1 | 2/2005 | Kohlstruck et al. | |
| 2005/0043562 A1 | 2/2005 | Kohlstruck et al. | |
| 2005/0043563 A1 * | 2/2005 | Kohlstruk et al. | ........... 560/345 |

FOREIGN PATENT DOCUMENTS

| | | |
|---|---|---|
| DE | 1 022 222 | 1/1958 |
| DE | 26 35 490 | 2/1977 |
| DE | 43 42 426 A1 | 6/1995 |
| DE | 196 27 552 A1 | 1/1998 |
| DE | 101 27 273 | 12/2002 |
| EP | 0 018 586 | 11/1980 |
| EP | 0 054 817 | 6/1982 |
| EP | 0 061 013 | 9/1982 |
| EP | 0 355 443 | 2/1990 |
| EP | 0 355 443 A2 | 5/1990 |
| EP | 0 566 925 | 10/1993 |
| EP | 0 566 925 A2 | 10/1993 |
| EP | 0 568 782 | 11/1993 |
| EP | 0 657 420 | 6/1995 |
| EP | 0 990 644 | 4/2000 |
| EP | 1 512 682 A1 | 3/2005 |

* cited by examiner

Primary Examiner—Daniel M Sullivan
Assistant Examiner—Sudhakar Katakam
(74) Attorney, Agent, or Firm—Oblon, Spivak, McClelland, Maier & Neustadt, P.C.

(57) ABSTRACT

Cycloaliphatic diisocyanates can be prepared continuously and phosgene-free by reacting at least one cycloaliphatic diamine with at least one carbonic acid derivative and at least one alcohol to give a cycloaliphatic diurethane; freeing the cycloaliphatic diurethane of a low boiler, a medium boiler and mixtures thereof; thermally cleaving the cycloaliphatic diurethane in a cleavage apparatus to give a cycloaliphatic diisocyanate and a cleavage residue; continuously discharging a portion of the cleavage residue from the cleavage apparatus; removing the high boiler components from the discharge to obtain a purified discharge; reurethanizing the purified discharge with alcohol to obtain a reurethanized discharge; and recycling the reurethanized discharge into the process.

49 Claims, No Drawings

MULTISTAGE CONTINUOUS PREPARATION OF CYCLOALIPHATIC DISOCYANATES

BACKGROUND OF THE INVENTION

1. Field of the Invention

The present invention relates to a multistage process for continuous and phosgene-free preparation of a cycloaliphatic diisocyanate.

2. Description of the Related Art

The synthetic access route to isocyanates may be via a series of different routes. The variant for industrial scale preparation of isocyanates which is the oldest and still predominates today is what is known as the phosgene route. This process is based on the reaction of amines with phosgene. A disadvantage of the phosgene process is the use of phosgene which, as a consequence of its toxicity and corrosivity, places particularly high requirements on its handling on the industrial scale.

There are several processes which avoid the use of phosgene for preparing isocyanates on the industrial scale. The term phosgene-free process is frequently used in connection with the conversion of amines to isocyanates using alternative carbonylating agents, for example urea or dialkyl carbonate (EP 18 586, EP 355 443, U.S. Pat. No. 4,268,683, EP 990 644).

The urea route is based on the urea-mediated conversion of diamines to diisocyanates via a two-stage process. In the first step, a diamine is reacted with alcohol in the presence of urea or urea equivalents (for example alkyl carbonates, alkyl carbamates) to give a diurethane which typically passes through an intermediate purification stage and is then thermally cleaved in the second step to diisocyanate and alcohol (EP 355 443, U.S. Pat. Nos. 4,713,476, 5,386,053). Alternatively, the actual urethane formation may also be preceded by the separate preparation of a diurea by selectively reacting the diamine with urea (EP 568 782). Also conceivable is a two-stage sequence consisting of partial reaction of urea with alcohol in the first and subsequent metering in and urethanization of the diamine in the second step (EP 657 420).

The thermal cleavage of urethanes to the corresponding isocyanates and alcohols has been known for some time and can be carried out either in the gas phase at high temperatures or at relatively low temperatures in the liquid phase. However, a problem in both procedures is that the thermal stress inevitably also causes undesired side reactions to take place which firstly reduce the yield and secondly lead to the formation of resinifying by-products which considerably disrupt the course of an industrial process as a result of deposits and blockages in reactors and workup apparatus.

There has therefore been no shortage of suggestions of chemical and process technology measures to achieve yield improvements and limit the undesired by-product formation. For instance, a series of documents describes the use of catalysts which accelerate the cleavage reaction of the urethanes (DE 10 22 222, U.S. Pat. No. 3,919,279, DE 26 35 490). Indeed, it is entirely possible in the presence of suitable catalysts, which are a multitude of basic, acidic and also organometallic compounds, to increase the isocyanate yield in comparison to the uncatalyzed variant. However, the formation of undesired by-products can also not be prevented by the presence of a catalyst. The same applies to the additional use of inert solvents, as recommended in U.S. Pat. No. 3,919,279 and DE 26 35 490, in order to ensure uniform distribution of the heat supplied and of the catalyst in the reaction medium. However, the use of solvents boiling under reflux fundamentally has the consequence of a reduction in the space-time yield of isocyanates and is additionally hindered with the disadvantage of additional high energy demands.

Examples which are cited in EP 54 817 for thermal catalyzed cleavage of monourethanes describe the partial discharge of the reaction mixture to remove resinifying by-products formed in the course of the urethane cleavage. This procedure serves to prevent deposits and blockages in reactors and workup units. There are no indications which point to a yield-increasing utilization of the partial discharge. EP 61 013 describes a similar approach to a solution, in which the thermolysis is in this case carried out in the presence of solvents whose purpose is apparently to better absorb the involatile by-products. Here also, the partial discharge is not utilized for the purposes of yield optimization.

EP 355 443 discloses that a yield increase can be achieved when the higher molecular weight by-products which can and cannot be utilized and are formed in the cleavage reactor during the cleavage of diurethanes, to ensure a disruption-free and selective reaction, are discharged substantially continuously out of the reactor and subsequently converted for the most part in the presence of alcohol and then recycled into the diurethane preparation. The procedure described is associated with high energy demands, since nonutilizable by-products are removed from the effluent of the diurethane preparation by distillation, and all of the diurethane has to be evaporated. In contrast to EP 355 443, the urethanization effluent in the process of EP 566 925 is divided into two substreams of which only one is freed by distillation of its high-boiling, nonutilizable by-products, before the combined diurethane streams are fed to the deblocking reaction in the cleavage reactor. In addition, the continuous cleavage reactor discharge in EP 566 925 is recycled directly, i.e. without a reurethanization step, into the diurethane synthesis.

The preparation of the diurethanes in a one-pot reaction from urea, diamine and dialcohol with simultaneous removal of ammonia is common practice and is described in a series of patents (EP 18 568, EP 355 443, EP 566 925). A disadvantage is that the simultaneous reaction of urea, alcohol and diamine inevitably results in large amounts of by-products being formed which impair the selectivity of the reaction and which have to be removed before the thermal deblocking of the diurethanes. EP 568 782 therefore claims a continuous process for preparing (cyclo)aliphatic diisocyanates which comprises essentially three main steps, of which the first describes the formation of bisureas, the second the formation of diurethanes from the bisureas and the third the cleavage of the diurethanes in the liquid phase to give the desired diisocyanates—in other words, the diurethane is prepared in two separate stages. According to the teaching of EP 568 782, the effluent of the reaction sequence composed of bisurea formation and subsequent diurethane synthesis is initially freed distillatively of low and medium boilers such as alcohols, carbamates and carbonates, and the high boilers in the urethane are then removed by short-path evaporation. The diurethane is deblocked thermally and a portion of the dissociation residue is continuously discharged, reurethanized with alcohol and recycled back into the diurethane synthesis stage.

SUMMARY OF THE INVENTION

This and other objects have been achieved by the present invention the first embodiment of which includes a multistage process for continuously preparing a cycloaliphatic diisocyanate, comprising:

reacting at least one cycloaliphatic diamine with at least one carbonic acid derivative and at least one alcohol to give a cycloaliphatic diurethane;

freeing the cycloaliphatic diurethane of a compound selected from the group consisting of a low boiler, a medium boiler and mixtures thereof;

thermally cleaving the cycloaliphatic diurethane in a cleavage apparatus to give a cycloaliphatic diisocyanate and a cleavage residue;

continuously discharging a portion of the cleavage residue from the cleavage apparatus;

removing the high boiler components from the discharge to obtain a purified discharge;

reurethanizing the purified discharge with alcohol to obtain a reurethanized discharge; and recycling the reurethanized discharge into the process.

In another embodiment, the present invention provides a multistage process for continuously preparing a cycloaliphatic diisocyanate, comprising:

a) reacting at least one cycloaliphatic diamine of the formula (II)

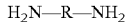
H$_2$N—R—NH$_2$ wherein R is a bivalent cycloaliphatic hydrocarbon radical having from 4 to 18 carbon atoms, the two nitrogen atoms being bonded directly to at least one hydrocarbon cycle and at least 3 carbon atoms being disposed between them, with urea and in the presence of at least one alcohol of the formula (III)

R$^1$—OH wherein R$^1$ is a radical as remains after removal of the hydroxyl group from a primary or secondary (cyclo)aliphatic alcohol having from 3 to 8 carbon atoms, in the absence or presence of a catalyst, to give at least one crude cycloalkylenebisurea of the formula (IV)

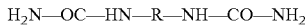
H$_2$N—OC—HN—R—NH—CO—NH$_2$ wherein R is a bivalent cycloaliphatic hydrocarbon radical having from 4 to 18 carbon atoms, with the proviso that the two nitrogen atoms flanking the two Rs bonded directly to a hydrocarbon cycle and at least 3 carbon atoms are disposed between them, and simultaneously continuously removing the formed ammonia;

b) converting said crude cycloalkylenebisurea in a second reactor using said alcohol of the formula (III) used in a) as a solvent while continuously driving off the released ammonia to give cycloalkylenediurethane of the formula (V)

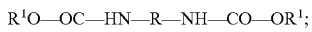
R$^1$O—OC—HN—R—NH—CO—OR$^1$;

wherein R is as defined in formula (IV) and R$^1$ is as defined in formula (III), to obtain a reaction mixture containing said alcohol, a dialkyl carbonate and/or alkyl carbamate;

c) removing the alcohol, the dialkyl carbonates and/or alkyl carbamates from said resulting reaction mixture, and recycling said alcohol into the reaction stage a);

d) fully or partially dispensing with a removal of any high-boiling residue present in said reaction mixture;

e) continuously and thermally cleaving the reaction mixture comprising the diurethane purified by steps c) and d) without solvent in the presence of a catalyst, at a temperature of from 180 to 280° C., and under a pressure of from 0.1 to 200 mbar, in such a way that a portion of from 10 to 60% by weight of the reaction mixture, based on the feed, is constantly discharged; thereby obtaining at least one cleavage product;

f) separating the cleavage product by rectification into crude cycloaliphatic diisocyanate and alcohol;

g) purifying the crude cycloaliphatic diisocyanate by distillation, to obtain a purified product fraction which is isolated;

h) separating a bottoms discharge from e) into a material-of-value stream and a waste stream, and discharging the waste stream which is rich in high boiler components from the process and disposing thereof;

i) reacting the material-of-value stream from h) with the alcohol from f) in the presence or absence of a catalyst within from 1 to 150 min, at a temperature of from 20 to 200° C., and a pressure of from 0.5 to 20 bar, and the molar ratio of NCO groups of the material-of-value stream to OH groups in the alcohol is up to 1:100;

j) continuously discharging a portion of the bottoms fraction of the purification by distillation g) and conducting said portion into the cleavage reaction e) and/or into the urethanization stage i);

k) optionally, recycling the top fraction obtained in the purification by distillation of the crude cycloaliphatic diisocyanate into the urethanization stage i); and l) recycling the reurethanized stream from i) into stage b) and/or c);

thereby obtaining a cycloaliphatic diisocyanate of the formula (I)

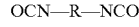
OCN—R—NCO wherein R is a bivalent cycloaliphatic hydrocarbon radical having from 4 to 18 carbon atoms, with the proviso that the two isocyanate groups are bonded directly to a hydrocarbon cycle and at least 3 carbon atoms are disposed between the two isocyanate groups.

DETAILED DESCRIPTION OF THE INVENTION

It has been found that, surprisingly, when cycloaliphatic diamines are used, it is advantageous to prepare the cycloaliphatic diurethanes by two-stage reaction of cycloaliphatic diamines with alcohol and urea, thus proceeding via bisurea. It is further advantageous to free the cycloaliphatic diurethanes of low and medium boilers, to thermally cleave the purified cycloaliphatic diurethanes to release the desired cycloaliphatic diisocyanate, to continuously discharge a portion of the cleavage residue from the cleavage apparatus and remove from it high boiler components. In addition, it has been found to be advantageous to reurethanize the purified discharge with alcohol and to recycle it into the process. It has been found that this method firstly realizes a comparatively low steady-state concentration of high boiler components over the entire sequence of diurethane synthesis, diurethane purification and diurethane cleavage, so that deposits, which are promoted in particular by the high boiler components which are highly viscous by nature, can be substantially avoided. This method also ensures good plant availability and good process yield even in the long term. Secondly, the high boiler removal downstream of the thermal cleavage reaction has the advantage that, in comparison to the customary procedure in which the high boilers are removed before the diurethane cleavage, the amount of diurethane to be converted to the vapor phase is significantly reduced. This allows capital and energy costs to be reduced.

The present invention provides a multistage process for continuously preparing cycloaliphatic diisocyanates, by reacting cycloaliphatic diamines with carbonic acid derivatives and alcohols to give cycloaliphatic diurethanes. Subsequently the diurethanes are thermally cleaved to give cycloaliphatic diisocyanates. The formation of the diurethanes is performed in two stages. The diurethane freed of low and medium boilers is thermally cleaved to release the desired diisocyanate. A portion of the cleavage residue is continuously discharged from the cleavage apparatus. The high boiler components are removed from the cleavage apparatus and the purified discharge is reurethanized with alcohol and recycled into the process.

The present invention also provides a multistage process for continuously preparing cycloaliphatic diisocyanates of the formula (I)

OCN—R—NCO wherein R is a bivalent cycloaliphatic hydrocarbon radical having from 4 to 18, preferably from 5 to 15, carbon atoms, with the proviso that the two isocyanate groups are bonded directly to a hydrocarbon cycle and at least 3 carbon atoms are disposed between them, by reacting cycloaliphatic diamines with carbonic acid derivatives and alcohols to give diurethanes and thermally cleaving them, wherein a) cycloaliphatic diamines of the formula (II)

$H_2N$—R—$NH_2$ wherein R is a bivalent cycloaliphatic hydrocarbon radical having from 4 to 18, preferably from 5 to 15, carbon atoms, the two nitrogen atoms being bonded directly to at least one hydrocarbon cycle and at least 3 carbon atoms being disposed between them, are reacted with urea and in the presence of alcohols of the formula (III)

$R^1$—OH wherein $R^1$ is a radical as remains after removal of the hydroxyl group from a primary or secondary (cyclo)aliphatic alcohol having from 3 to 8 carbon atoms, in the absence or presence of catalysts, to give cycloalkylenebisureas of the formula (IV)

$H_2N$—OC—HN—R—NH—CO—$NH_2$ wherein R is a bivalent cycloaliphatic hydrocarbon radical having from 4 to 18, preferably from 5 to 15, carbon atoms, with the proviso that the two nitrogen atoms flanking the two Rs are bonded directly to a hydrocarbon cycle and at least 3 carbon atoms are disposed between them, and the ammonia formed is simultaneously removed continuously;

b) the resulting crude cycloalkylenebisurea is converted in a second reactor using the alcohol of the formula (III) used in a) as a solvent while continuously driving off the ammonia released to give cycloalkylenediurethane of the formula (V)

$R^1O$—OC—HN—R—NH—CO—$OR^1$;

c) the alcohol, the dialkyl carbonates and/or alkyl carbamates are removed from the resulting reaction mixture, and the alcohol is recycled into the reaction stage a);

d) a removal of any high-boiling residues present in the resulting reaction mixture is fully or partially dispensed with;

e) the reaction mixture comprising the diurethanes purified by steps c) and d) is continuously and thermally cleaved in the presence of a catalyst and without solvent, at temperatures of from 180 to 280° C., preferably from 200 to 260° C., and under a pressure of from 0.1 to 200 mbar, preferably from 0.2 to 100 mbar, in such a way that a portion of the reaction mixture of from 10 to 60% by weight based on the feed, preferably from 15 to 45% by weight based on the feed, is constantly discharged;

f) the cleavage products are separated by rectification into crude diisocyanate and alcohol;

g) the crude cycloaliphatic diisocyanate, purified by distillation, and the pure product fraction are isolated;

h) the bottoms discharge from e) is separated into a material-of-value stream and a waste stream, and the waste stream which is rich in high boiler components is discharged from the process and disposed of;

i) the material-of-value stream from h) is reacted with the alcohol from f) in the presence or absence of catalysts within from 1 to 150 min, preferably from 3 to 60 min, at temperatures of from 20 to 200° C., preferably from 50 to 170° C., and a pressure of from 0.5 to 20 bar, preferably from 1 to 15 bar, and the molar ratio of NCO groups to OH groups is up to 1:100, preferably 1:20 and more preferably 1:10;

j) a portion of the bottoms fraction of the purification by distillation g) is continuously discharged and conducted into the cleavage reaction e) and/or into the urethanization stage i);

k) optionally, the top fraction obtained in the purification by distillation of the crude cycloaliphatic diisocyanate is likewise recycled into the urethanization stage i);

l) the reurethanized stream from i) is recycled into stage b) and/or c).

In the process according to the present invention, cycloaliphatic diisocyanates can be prepared continuously, without any problem and in very good yield. What is advantageous in the multistage process according to the present invention is in particular the fact that even when cycloaliphatic diamines of the formula (II) are used as a starting material for the continuous diisocyanate synthesis, deposits, which are supported in particular by the high boiler components which are highly viscous by nature, can be substantially prevented and good plant availability and good process yield are ensured even in the long term. It is a further advantage of the multistage process according to the present invention that it allows the amount of the diurethane to be converted to the vapor phase to be reduced to a minimum and in this way restricts the necessary energy demands.

a) To prepare the cycloalkylenebisureas of the formula (IV) in reaction stage a), the cycloaliphatic diamines of the formula (II) are reacted with urea in the presence of an alcohol of the formula (III), optionally also mixtures of such alcohols, in a reactor at from 100 to 145° C. and a pressure of from 0.7 to 1.8 bar, in the course of which the ammonia formed is driven out continuously. The reaction temperature includes all values and subvalues therebetween, especially including 105, 110, 115, 120, 125, 130, 135 and 140° C. The pressure includes all values and subvalues therebetween, especially including 0.8, 0.9, 1, 1.1, 1.2, 1.3, 1.4, 1.5, 1.6, 1.7 bar. The reaction is affected preferably in a distillation reactor, in which case the reactants are introduced in a molar diamine:urea:alcohol ratio of 1:2.0 to 2.4: 3 to 10 continuously to the uppermost tray and the ammonia released is driven out by alcohol vapors which are introduced in the bottom of the distillation reactor. The residence time required is from 4 to 10 hours, preferably from 5 to 9 hours. The residence time includes all values and subvalues therebetween, especially including 4.5, 5, 5.5, 6, 6.5, 7, 7.5, 8, 8.5, 9 and 9.5 hours. The amount of alcohol introduced in the bottom to drive out the ammonia is from 0.05 to 3 kg/kg, preferably from 0.1 to 1 kg/kg, of bisurea, and the amount of alcohol thus introduced is drawn off at the top together with the ammonia formed, freed of residual ammonia after partial condensation in an alcohol recovery column, and recycled into the bottom. The amount of alcohol introduced in the bottom includes all values and subvalues therebetween, especially including 0.1, 0.5, 1, 1.5, 2, 2.5 kg/kg.

b) The crude cycloalkylenebisurea dissolved in alcohol and obtained in the bottom of the distillation reactor is conducted continuously into a second reactor in which the conversion to the diurethane is effected at elevated temperature and elevated pressure, in the course of which ammonia is again released and has to be removed from the reaction mixture for reasons of chemical equilibrium. The further conversion of the crude cycloalkyleneurea from a) is effected preferably in a pressure distillation reactor and at a molar ratio of bisurea to alcohol of 1:5 to 12. The molar ratio of bisurea to alcohol includes all values and subvalues therebetween, especially including 1:5.5, 1:6, 1:6.5, 1:7, 1:7.5, 1:8, 1:8.5, 1:9, 1:9.5, 1:10, 1:10.5, 1:11, 1:11.5. The stream from a) is conducted preferably continuously to the uppermost tray of the pressure distillation reactor. The reaction takes place in the absence or presence of catalysts at reaction temperatures of from 140 to 270° C., preferably from 160 to 250° C., and under a pressure which is from 5 to 20 bar, preferably from 7 to 15 bar, within from 2 to 20 hours, preferably from 8 to 15 hours. The reaction temperature includes all values and subvalues therebetween, especially including 150, 160, 170, 180, 190, 200, 210, 220, 230, 240, 250 and 260° C. The pressure includes all values and subvalues therebetween, especially including 7.5, 8, 8.5, 9, 9.5, 10, 10.5, 11, 11.5, 12, 12/5, 13, 13.5, 14 and 14.5 bar. The reaction time includes all values and subvalues therebetween, especially including 3, 4, 5, 6, 7, 8,9, 10, 11, 12, 13, 14, 15, 16, 17, 18 and 19 hours. The continuous driving-out of the ammonia released is supported by alcohol vapors which are introduced in the bottom of the pressure distillation reactor and are appropriately generated in an evaporator mounted at the top of the column.

To increase the reaction rate, the diurethanes may be prepared in the presence of catalysts. Suitable catalysts are inorganic or organic compounds which contain one or more, preferably a cation of, metals or groups IA, IB, IIA, IIB, IIIA, IIIB, IVA, IVB, VA, VB, VIB, VIIB and VIIIB of the Periodic Table, defined in accordance with Handbook of Chemistry and Physics 14th Edition, published by Chemical Rubber Publishing Co. 2310 Superior Ave. N.E. Cleveland, Ohio, for example halides such as chlorides and bromides, sulfates, phosphates, nitrates, borates, alkoxides, phenoxides, sulfonates, oxides, oxide hydrates, hydroxides, carboxylates, chelates, carbonates and thio- or dithiocarbamates. Examples include the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Examples of typical catalysts include the following compounds: lithium ethoxide, lithium butoxide, sodium methoxide, potassium tert-butoxide, magnesium ethoxide, calcium methoxide, tin(II) chloride, tin(IV) chloride, lead acetate, aluminum trichloride, bismuth trichloride, copper(II) acetate, copper(II) chloride, zinc chloride, zinc octoate, titanium tetrabutoxide, vanadium trichloride, vanadium acetylacetonate, manganese(II) acetate, iron(II) acetate, iron(III) acetate, iron oxalate, cobalt chloride, cobalt naphthenate, nickel chloride, nickel naphthenate and mixtures thereof. The catalysts may optionally also be used in the form of their hydrates or ammoniates.

Starting compounds for the process according to the present invention are diamines of the formula (II) which has already been mentioned above, alcohols of the formula (III) which has already been mentioned above, and also urea. Suitable diamines of the formula (II) are, for example, 1,4 diaminocyclohexane, 4,4'-dicyclohexylmethanediamine, 2,4-dicyclohexylmethanediamine, 2,2'-dicyclohexylmethanediamine and isomeric cycloaliphatic diamines, and also perhydrogenated diphenylmethanediamine. As a result of the preparation, diphenylmethanediamine (MDA) occurs as an isomer mixture of 4,4'-, 2,4- and 2,2'-MDA (see, for example, DE 101 27 273). Perhydrogenated diphenylmethanediamine is obtained by fully hydrogenating MDA and is accordingly a mixture of isomeric dicyclohexylmethanediamines ($H_{12}$MDA), i.e. 4,4'-, 2,4- and 2,2'-$H_{12}$MDA and possibly small amounts of (semi)aromatic MDA which has not been fully converted. The diamines of the formula (II) used are preferably 4,4'-dicyclohexylmethanediamine, 2,4-dicyclohexylmethanediamine and 2,2'-dicyclohexylmethanediamine, and also any mixtures of at least two of these isomers. In addition, diamines may also be used which deviate from the formula (II). Examples include 1,3- and 1,4-diaminomethylcyclohexane, 1,6-hexanediamine, 2,2,4- or 2,4,4-trimethyl-1,6-hexanamine and 3-aminomethyl-3,5,5-trimethylcyclohexylamine. However, preference is not given to using amines which deviate from the formula (II).

Suitable alcohols of the formula (III) are any aliphatic or cycloaliphatic alcohols which have a boiling point below 190° C. under atmospheric pressure. Examples include $C_1$-$C_6$-alkanols, for example methanol, ethanol, 1-propanol, 1-butanol, 2-butanol, 1-hexanol or cyclohexanol. The alcohol used is preferably 1-butanol.

In the course of the conversion of the reaction mixture, ammonia is released, whose removal from the reaction equilibrium has been found to be advantageous. When ammonia is discharged from the reactor, care has to be taken that the wall temperatures of the reactor and of the discharge tube are above 60° C., so that deposition of ammonium carbamate, which is formed in minimal amounts from ammonia and carbon dioxide by decomposition of urea, can be prevented. It has been found to be useful, for example, to carry out the reaction in a pressure distillation reactor, in which case the reaction mixture is conducted in countercurrent to alcohol vapors introduced in the bottom and in this way such intensive mixing of the liquid proceeds on the trays that they each virtually correspond to a battery stage. The vaporous mixture of alcohol and ammonia which is withdrawn at the top may, preferably under the pressure of the pressure distillation reactor and without condensing it beforehand, be conducted into a distillation column, in order, from the ammonia, to obtain free alcohol which is recycled into the bottom of the pressure distillation reactor and of the column. In order to prevent fouling of the reflux condenser with ammonium carbamate, an appropriate proportion of alcohol is permitted therein to set the temperature at the top to at least 60° C.

c) The excess alcohol, the dialkyl carbonates, if they have been formed, or alkyl carbamates or mixtures of at least two of these components are removed in one stage or advantageously in two stages. At the first stage, the reaction mixture is decompressed from the pressure level of reaction stage b) to a pressure of 1-500 mbar, preferably 2-150 mbar, and in this way separated into gaseous vapors which contain the predominant amount of alcohol and also any dialkyl carbonates and/or alkyl carbamates, and into a liquid effluent. The pressure includes all values and subvalues therebetween, especially including 50, 100, 150, 200, 250, 300, 350, 400 and 450 mbar. In the second stage, the liquid effluent is freed of any remaining residual butanol and also medium boilers such as dialkyl carbonates and/or alkyl carbamates by thin-film evaporation at 180-250° C., preferably 200-230° C., and a pressure of 0.1-20 mbar, preferably 1-10 mbar, so that the residue consists substantially of the monomeric diurethane, and in some cases high-boiling oligomers. The temperature includes all values and subvalues therebetween, especially including 190, 200, 210, 220, 230 and 240° C. The pressure includes all values and subvalues therebetween, especially including 0.5, 1, 2, 4, 6, 8, 10, 12, 14, 16, and 18 mbar. The vapors may, after further distillative purification, be recycled into reaction stage a). Recycling of the dialkyl carbonates and/or alkyl carbamates into reaction stage b) is possible but not required.

d) Preference is given to dispensing with any removal of any high boilers present in the reaction mixture from stage c). However, if the separation described under h) of the bottoms discharge from stage e) is carried out only with one substream, i.e. partially, it may be advantageous to follow the routes for high boiler removal which are described below:

Optionally, the liquid stream from step c) which contains the monomeric diurethanes and any high-boiling oligomers and is obtained after the removal of low and medium boilers may be separated, preferably with the aid of a thin-film or short-path evaporator, at a temperature of 180-260° C., preferably 200-240° C., and under a pressure of 0.01-10 mbar, preferably 0.02 5 mbar, by distillation into a material-of-value stream which contains the monomeric diurethanes and the lower-boiling by-products and a nondistillable by-product stream. The temperature includes all values and subvalues therebetween, especially including 190, 200, 210, 220, 230, 240 and 250° C. The pressure includes all values and subvalues therebetween, especially including 0.05, 0.1, 0.5, 1, 2, 3, 4, 5, 6, 7, 8 and 9 mbar. The nondistillable by-product stream which contains the high-boiling components is discharged from the preparative process and is typically discarded as a residue whose material cannot be utilized.

Optionally, the stream from stage c) which contains any high-boiling oligomers, before its above-described distillative purification, may also be divided into two substreams of which one is fed directly to the deblocking reaction (see e)) and the other initially passes through the high boiler removal just described.

e) The material-of-value stream from stage c) and optionally from stage d) which contains the monomeric diurethanes and the lower-boiling by-products is partly and continuously thermally cleaved in a suitable apparatus, without solvents in the liquid phase in the presence of catalysts at temperatures of 180-280° C., preferably 200-260° C., and under a pressure of 0.1-200 mbar, preferably 0.2-100 mbar. The temperature includes all values and subvalues therebetween, especially including 190, 200, 210, 220, 230, 240, 250, 260 and 270° C. The pressure includes all values and subvalues therebetween, especially including 0.5, 1, 5, 10, 20, 40, 60, 80, 100, 120, 140, 160 and 180 mbar. The conversion of diurethane to diisocyanate in the apparatus for thermal cleavage may, depending on the diurethane used, be selected substantially freely and is typically within the range of 10-95% by weight, preferably 35-85% by weight of the diurethane feed. The conversion of diurethane to diisocyanate includes all values and subvalues therebetween, especially including 20, 30, 40, 50, 60, 70, 80 and 90% by weight. The uncleaved proportion of the reaction mixture which contains unconverted diurethanes, high-boiling by-products and other reutilizable and nonutilizable by-products is continuously discharged. The amount of the discharge is governed, inter alia, by the desired conversion and the desired capacity of the cleavage reaction and can be easily determined experimentally. It is typically 10-60% by weight, preferably 15-45% by weight, based on the feed. The amount of discharge includes all values and subvalues therebetween, especially including 15, 20, 25, 30, 35, 40, 45, 50, and 55% by weight.

Useful catalysts for chemically cleaving the diurethanes are, for example, the aforementioned inorganic and organic compounds which catalyze urethane formation. Preference is given to using chlorides of zinc, tin or copper, and also zinc oxides, manganese oxides, iron oxides or cobalt oxides, in which case the catalyst is metered into the mass flow from the purification stage c) and optionally d), before it is fed into the cleavage, as a 0.01-25% by weight, preferably 0.05-10% by weight, solution or suspension, into the alcohol which is also used for urethane preparation, in an amount of 5-400 ppm, preferably 10-100 ppm. The amount of catalyst in the alcohol includes all values and subvalues therebetween, especially including 0.5, 1, 2, 4, 6, 8, 10, 12, 14, 16, 18, 20, 22 and 24% by weight. The amount of catalyst which is metered into the mass flow includes all values and subvalues therebetween, especially including 50, 100, 150, 200, 250, 300 and 350 ppm.

Suitable cleavage apparatus is, for example, cylindrical cleavage reactors, for example tubular furnaces or preferably evaporators such as falling-film, thin-film or bulk evaporators, selected from Robert evaporators, Herbert evaporators, Caddle-type evaporators, Oskar evaporators and heating cartridge evaporators.

In principle, the main concern is to keep the average residence time of isocyanate groups, which are inevitably released when the alcohol is deblocked, in the cleavage zone very low and thus to limit undesired side reactions to a minimum.

Preference is given to carrying out the cleavage in a combined cleavage and rectification column, which is equipped for the energy supply in the bottom with a falling-film evaporator, in the lower third with a unit for additional energy input or for energy recovery, in the upper third with a unit to remove preferably crude diisocyanate and at the top with a condenser for the reflux and the removal of pure alcohol.

f) The cleavage products which are formed in the thermal cleavage and are composed in particular of alcohol, diisocyanate and partially cleaved diurethanes are separated by rectification at 95-260° C., preferably 110-245° C., and a pressure of 0.5-250 mbar, preferably 1-100 mbar, into alcohol and into a crude diisocyanate mixture, consisting of cycloaliphatic diisocyanate, partially cleaved cycloaliphatic diisocyanate and in some cases small amounts of cycloaliphatic diurethane. This separation may be carried out, for example, in the cleavage colum of the abovementioned combined cleavage and rectification column. The temperature of the rectification includes all values and subvalues therebetween, especially including 100, 110, 120, 130, 140, 150, 160, 170, 180, 190, 200, 210, 220, 230, 240, and 250° C. The pressure includes all values and subvalues therebetween, especially including 20, 40, 60, 80, 100, 120, 140, 160, 180, 200, 220 and 240 mbar.

g) The crude mixture which is preferably obtained by rectification, consisting of cycloaliphatic diisocyanate, partially cleaved cycloaliphatic diurethane and in some cases small fractions of cycloaliphatic diurethane, is purified by distillation at a temperature of 95-260° C., preferably 110-245° C., and under a pressure of 0.5-150 mbar, preferably 1-75 mbar, and the resulting fractions are recycled or isolated as a pure product. The temperature of the distillation includes all values and subvalues therebetween, especially including 100, 110, 120, 130, 140, 150, 160, 170, 180, 190, 200, 210, 220, 230, 240, and 250° C. The pressure includes all values and subvalues therebetween, especially including 20, 40, 60, 80, 100, 120 and 140 mbar.

h) The bottoms discharge from the deblocking stage e) is separated into a material-of-value stream and a waste stream, and the waste stream which is rich in high boiler components is discharged from the process and discarded. The two streams are separated preferably by distillation with the aid of a thin-film or short-path evaporator, at a temperature of 180-270° C., preferably 200-250° C., and under a pressure of 0.01-10 mbar, preferably 0.02-5 mbar. The temperature of the distillation includes all values and subvalues therebetween, especially including 190, 200, 210, 220, 230, 240, 250 and 260° C. The pressure includes all values and subvalues therebetween, especially including 0.05, 0.1, 0.5, 1, 1.5, 2, 2.5, 3, 3.5, 4, 4.5, 5, 5.5, 6, 6.5, 7, 7.5, 8, 8.5, 9, and 9.5 mbar. The material-of-value stream which contains the monomeric diurethanes and the lower-boiling by-products is obtained as the distillate. The waste stream which is rich in high-boiling components is obtained as the residue and is discharged from the preparative process and typically discarded as a nonutilizable material. Alternatively, but not preferably, the separation into material-of-value and waste material may also be effected by extraction. An example of a suitable extractant is supercritical carbon dioxide.

Optionally, the bottoms discharge may also be divided before the above-described distillative purification into two substreams of which one is fed directly to the reurethanization (see i)). The division of the two streams may be effected in a ratio of from 99:1 to 1:99, preferably from 99:5 to 5:95.

i) The material-of-value stream from stage h) is combined with the alcohol from the rectification stage f), in a molar ratio of NCO groups to OH groups of up to 1:100, preferably 1:20 and more preferably 1:10, and the reaction mixture is converted, in the presence or absence of catalysts, within 1-150 min, preferably 3-60 min, at temperatures of 20-200° C., preferably 50-170° C., and a pressure of 0.5-20 bar, preferably 1-15 bar. The molar ratio of NCO to OH groups includes all values and subvalues therebetween, especially including 1:10, 1:20, 1:30, 1:40, 1:50, 1:60, 1:70, 1:80 and 1:90. The conversion pressure includes all values and subvalues therebetween, especially including 1, 2, 4, 6, 8, 10, 12, 14, 16, and 18 bar. The conversion time includes all values and subvalues therebetween, especially including 10, 20, 30, 40, 50, 60, 70, 80, 90, 100, 110, 120, 130 and 140 min. The conversion temperature includes all values and subvalues therebetween, especially including 40, 60, 80, 100, 120, 140, 160 and 180° C. The reaction may be carried out in a continuous tank battery or in a tubular reactor. Useful catalysts are in principle all catalysts which support the NCO/OH reaction. Examples include tin octoate, dibutyltin laurate, tin dichloride, zinc dichloride, copper chloride, copper dichloride, iron dichloride, iron trichloride and triethylamine.

j) A portion of the bottoms fraction of the purifying distillation g) is continuously discharged and optionally recycled into the deblocking stage e) or into the urethanization stage g). Preference is given to recycling into the urethanization stage. The amount of the discharge is 0.1-50% by weight, preferably 0.2-25% by weight, of the feed of crude diisocyanate into the purifying distillation stage. The amount of discharge includes all values and subvalues therebetween, especially including 0.5, 1, 5, 10, 15, 20, 25, 30, 35, 40, and 45% by weight.

k) The top fraction of the purifying distillation stage g) may be discarded or preferably recycled into the urethanization stage i). The amount of top fraction removed per unit time is 0.1-3% by weight, preferably 0.3-1% by weight, of the feed of crude diisocyanate into the purifying distillation. The amount of top fraction includes all values and subvalues therebetween, especially including 0.5, 1, 1.5, 2, and 2.5% by weight.

l) The stream from the urethanization stage i) is recycled into the low and medium boiler removal c) and/or the diurethane preparation b).

The multistage process according to the present invention for continuously preparing cycloaliphatic diisocyanates with recycling and discharge of the by-products allows, for distillable cycloaliphatic diisocyanates, a reaction which proceeds without disruption and with high selectivity to be ensured. The process according to the present invention is suitable in particular for preparing cycloaliphatic diisocyanates having from 4 to 18, preferably from 5 to 15, carbon atoms, such as 1,4-diisocyanatocyclohexane, 4,4'-dicyclohexylmethane diisocyanate (4,4'-$H_{12}$MDI), 2,2'-dicyclohexylmethane diisocyanate (2,2'-$H_{12}$MDI), 2,4'-dicyclohexylmethane diisocyanate (2,4'-$H_{12}$MDI) or else mixtures of the aforementioned isomeric dicyclohexylmethane diisocyanates ($H_{12}$MDI), as are obtained, for example, by the nature of the conversion of perhydrogenated MDA to $H_{12}$MDI. Very particular preference is given to preparing 4,4'-dicyclohexylmethane diisocyanate and any mixtures of 4,4'-$H_{12}$MDI, 2,4-$H_{12}$MDI and 2,2'-$H_{12}$MDI.

The cycloaliphatic diisocyanates prepared are excellently suited to preparing polymers containing urethane, isocyanurate, amide and/or urea groups by the polyisocyanate polyaddition process. They additionally find use for preparing polyisocyanate mixtures modified with urethane, biuret and/or isocyanurate groups. Such polyisocyanate mixtures of cycloaliphatic diisocyanates are used in particular for preparing high-value, light-resistant polyurethane coatings.

Having generally described this invention, a further understanding can be obtained by reference to certain specific examples which are provided herein for purposes of illustration only, and are not intended to be limiting unless otherwise specified.

EXAMPLES

Example 1

Preparation according to the present invention of dicyclohexylmethane diisocyanate ($H_{12}$MDI) from perhydrogenated diphenylmethanediamine and urea in the presence of n-butanol.

Every hour, the uppermost tray of a pressure distillation reactor was charged with 278.7 g of $H_{12}$MDA, 163.5 g of urea and 592 g of n-butanol, and the reaction mixture was boiled at 135° C. and an average residence time of 8 hours while continuously removing the ammonia released at normal pressure. The solution, obtained in the bottom of the distillation reactor, of bisurea in butanol was preheated to 190° C. using a heat exchanger, conducted to the uppermost tray of a pressure distillation reactor and reacted further at from 11 to 14 bar, 220° C. and with an average residence time of 10.5 h. In the bottom of the pressure distillation reactor, 536.9 g per hour of n butanol were fed in and the amount of alcohol drawn off together with the ammonia released was selected in such as way that it corresponded to the alcohol input in the bottom. The reactor effluent, together with the stream from the reurethanization, was subsequently freed of excess alcohol, low boilers and medium boilers in the flash vessel at 55 mbar with subsequent thin-film evaporation at 220° C. and 2 mbar, and the remaining 771.1 g/h of bis(4-butoxycarbonylaminocyclohexyl)methane ($H_{12}$MDU) were conducted as a melt (140° C.) into the circulation of the falling-film evaporator of the cleavage and rectification column, and the deblocking reaction was carried out at a temperature of 237° C. and a bottom pressure of 10 mbar in the presence of a steady-state concentration of tin dichloride of 14 ppm. The cleavage gases, $H_{12}$MDI and butanol, were condensed out in two condensers connected in series at 85° C. and −25° C. The resulting about 97% crude $H_{12}$MDI was fed to a purifying distillation where 317.2 g/h of H$_{12}$MDI having a purity of >99.5% were obtained, which corresponds to a yield of 91% based on the amine. 226.9 g/h of butanol were obtained as the top product of the cleavage and rectification column. To maintain constant mass within the cleavage and rectification column and avoid fouling and blockages of the cleavage apparatus, a substream was continuously discharged from the circuit and separated by means of a short-path evaporator at 230° C. and a pressure of 0.04 mbar into a high boiler-rich waste stream and a material-of-value stream. The 174.9 g/h of material-of-value stream were combined together with 23.7 g/h of material separated from the bottoms of the H$_{12}$MDI purifying distillation, and also the top product from the cleavage and rectification column, and reurethanized. The reurethanized material was fed to the flash vessel together with the reactor effluent of the diurethane preparation.

Example 2

Preparation according to the present invention of dicyclohexylmethane diisocyanate (H$_{12}$MDI) from perhydrogenated diphenylmethanediamine and urea in the presence of n-butanol—reurethanization in the presence of CuCl and recycling of the reurethanized material into the low boiler and medium boiler removal.

Every hour, the uppermost tray of a pressure distillation reactor was charged with 275.1 g of H$_{12}$MA, 162.9 g of urea and 590.1 g of n-butanol, and the reaction mixture was boiled while continuously removing the ammonia released at standard pressure, 135° C. and an average residence time of 8 hours. The solution, obtained in the bottom of the distillation reactor, of bisurea in butanol was preheated to 190° C. using a heat exchanger, conducted to the uppermost tray of a pressure distillation reactor and reacted further at from 11 to 14 bar, 220° C. and with an average residence time of 10.5 h. In the bottom of the pressure distillation reactor, 536 g per hour of n-butanol were fed in and the amount of alcohol drawn off together with the ammonia released was selected in such as way that it corresponded to the alcohol input in the bottom. The reactor effluent, together with the stream from the reurethanization, was freed at 220° C. and 2 mbar of excess alcohol, low and medium boilers in the flash vessel at 55 mbar with subsequent thin-film evaporation and the remaining 763.2 g/h of bis (4-butoxycarbonylaminocyclohexyl)methane (H$_{12}$MDU) were conducted as a melt (140° C.) into the circulation of the falling-film evaporator of the cleavage and rectification column, where the deblocking reaction was carried out at a temperature of 235° C. and a bottom pressure of 9 mbar in the presence of a steady-state concentration of tin dichloride of 16 ppm. The cleavage gases, H$_{12}$MDI and butanol, were condensed out in two condensers connected in series at 85 and −25° C. The resulting about 97% crude H$_{12}$MDI was fed to a purifying distillation to obtain 309.1 g/h of H$_{12}$MDI having a purity of >99.5%, which corresponds to a yield of 90% based on the amine. 226.4 g/h of butanol were obtained as the top product of the cleavage and rectification column. To maintain constant mass within the cleavage and rectification column and prevent fouling and blockages of the cleavage apparatus, a substream was continuously discharged from the circuit and divided in an 80:20 ratio, and the majority was separated by means of a short-path evaporator at 235° C. and a pressure of 0.05 mbar into a high boiler-rich waste stream and a material-of-value stream. The 129.45 g/h of material-of-value stream were combined with 22.7 g/h of material separated from the bottoms of the H$_{12}$MDI purifying distillation, and also the top product from the cleavage and rectification column and the unpurified substream from the discharge, and reurethanized in the presence of 100 ppm of CuCl. The reurethanized material was fed to the flash vessel together with the reactor effluent of the diurethane preparation.

German patent application 10 2004 022 626.1 filed May 7, 2004, is incorporated herein by reference.

Numerous modifications and variations on the present invention are possible in light of the above teachings. It is therefore to be understood that within the scope of the appended claims, the invention may be practiced otherwise than as specifically described herein.

What is claimed is:

1. A multistage process for continuously preparing a cycloaliphatic diisocyanate, comprising:
    reacting at least one cycloaliphatic diamine with at least one carbonic acid derivative and at least one alcohol to give a cycloaliphatic diurethane;
    freeing the cycloaliphatic diurethane of a compound selected from the group consisting of a low boiler, a medium boiler and mixtures thereof;
    thermally cleaving the cycloaliphatic diurethane in a cleavage apparatus to give a cycloaliphatic diisocyanate and a cleavage residue;
    continuously discharging a portion of the cleavage residue from the cleavage apparatus;
    removing the high boiler components from the discharge to obtain a purified discharge;
    reurethanizing the purified discharge with alcohol to obtain a reurethanized discharge; and
    recycling the reurethanized discharge into the process.

2. A multistage process for continuously preparing a cycloaliphatic diisocyanate, comprising:
    a) reacting at least one cycloaliphatic diamine of the formula (II)

wherein R is a bivalent cycloaliphatic hydrocarbon radical having from 4 to 18 carbon atoms, the two nitrogen atoms being bonded directly to at least one hydrocarbon cycle and at least 3 carbon atoms being disposed between them, with urea and in the presence of at least one alcohol of the formula (III)

wherein R$^1$ is a radical as remains after removal of the hydroxyl group from a primary or secondary (cyclo) aliphatic alcohol having from 3 to 8 carbon atoms, in the absence or presence of a catalyst, to give at least one crude cycloalkylenebisurea of the formula (IV)

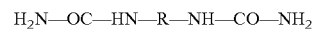

wherein R is a divalent cycloaliphatic hydrocarbon radical having from 4 to 18 carbon atoms,
    with the proviso that the two nitrogen atoms flanking the two Rs are bonded directly to a hydrocarbon cycle and at least 3 carbon atoms are disposed between them, and
    simultaneously continuously removing the formed ammonia;

b) converting said crude cycloalkylenebisurea in a second reactor using said alcohol of the formula (III) used in a) as a solvent while continuously driving off the released ammonia to give cycloalkylenediurethane of the formula (V)

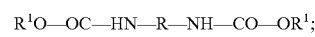

wherein R is as defined in formula (IV) and R¹ is as defined in formula (III), to obtain a reaction mixture containing said alcohol, a dialkyl carbonate and/or alkyl carbamate;

c) removing the alcohol, the dialkyl carbonates and/or alkyl carbamates from said resulting reaction mixture, and recycling said alcohol into the reaction stage a);

d) fully or partially dispensing with a removal of any high-boiling residue present in said reaction mixture;

e) continuously and thermally cleaving the reaction mixture comprising the diurethane purified by steps c) and d) without solvent in the presence of a catalyst, at a temperature of from 180 to 280° C., and under a pressure of from 0.1 to 200 mbar, in such a way that a portion of from 10 to 60% by weight of the reaction mixture, based on the feed, is constantly discharged; thereby obtaining at least one cleavage product;

f) separating the cleavage product by rectification into crude cycloaliphatic diisocyanate and alcohol;

g) purifying the crude cycloaliphatic diisocyanate by distillation, to obtain a purified product fraction which is isolated;

h) separating a bottoms discharge from e) into a material-of-value stream and a waste stream, and discharging the waste stream which is rich in high boiler components from the process and disposing thereof;

i) reacting the material-of-value stream from h) with the alcohol from f) in the presence or absence of a catalyst within from 1 to 150 mm, at a temperature of from 20 to 200° C., and a pressure of from 0.5 to 20 bar, and the molar ratio of NCO groups of the material-of-value stream to OH groups in the alcohol is up to 1:100;

j) continuously discharging a portion of the bottoms fraction of the purification by distillation g) and conducting said portion into the cleavage reaction e) and/or into the urethanization stage i);

k) optionally, recycling the top fraction obtained in the purification by distillation of the crude cycloaliphatic diisocyanate into the urethanization stage i); and l) recycling the reurethanized stream from i) into stage b) and/or c);

thereby obtaining a cycloaliphatic diisocyanate of the formula (I)

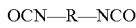

OCN—R—NCO wherein R is a bivalent cycloaliphatic hydrocarbon radical having from 4 to 18 carbon atoms, with the proviso that the two isocyanate groups are bonded directly to a hydrocarbon cycle and at least 3 carbon atoms are disposed between the two isocyanate groups.

3. The multistage process of claim 1 or 2, wherein the cycloaliphatic diamine is a member selected from the group consisting of 4,4'-dicyclohexylmethanediamine, an isomeric cycloaliphatic diamine and mixtures thereof.

4. The multistage process of claim 3, wherein the cycloaliphatic diamine is a member selected from the group consisting of 4,4'-dicyclohexylmethanediamine, 2,4-dicyclohexylmethanediamine, 2,2'-dicyclohexylmethanediamine, and mixtures thereof.

5. The multistage process of claim 1 or 2, wherein the cycloaliphatic diamine is 1,4-diaminocyclohexane.

6. The process of claim 2, wherein stage a) is carried out in a reactor at a temperature of from 100 to 145° C. and a pressure of from 0.7 to 1.8 bar.

7. The process of claim 2, wherein stage a) is carried out in a distillation reactor.

8. The process of claim 1, wherein the reaction in stage a) is effected in a molar ratio of diamine:urea:alcohol of from 1:2.0 to 2.4:3 to 10.

9. The process of claim 7, wherein, in stage a), the reactants are supplied continuously to the uppermost tray and the ammonia released is driven out by alcohol vapors which are introduced into the bottom of the distillation reactor.

10. The process of claim 2, wherein the residence time of the reactants in stage a) is from 4 to 10 hours.

11. The process of claim 2, wherein stage b) is carried out in a pressure distillation reactor.

12. The process of claim 2, wherein stage b) is conducted at a molar ratio of bisurea to alcohol of 1:5 to 12.

13. The process of claim 2, wherein the stream from a) is conducted continuously to the uppermost tray of the reactor of stage b).

14. The process of claim 2, wherein in stage b), conversion is effected at a reaction temperature of from 140 to 270° C. and under a pressure of from 5 to 20 bar.

15. The process of claim 2, wherein the reaction in stage b) takes place within from 2 to 20 hours.

16. The process of claim 2, wherein the reaction in stage a) and/or in stage b) is carried out in the presence of at least one catalyst.

17. The process of claim 2, wherein, in stages a) and b), alcohols having 1-6 carbon atoms are used.

18. The process of claim 2, wherein, in stages a) and b), butanol is used.

19. The process of claim 2, wherein stage c) is carried out in two stages.

20. The process of claim 19, wherein, at the first stage, the reaction mixture is decompressed from the pressure level of reaction stage b) to a pressure of from 1 to 500 mbar.

21. The process of claims 19 or 20, wherein, in the second step, the liquid effluent is freed of any residual alcohol present and also of medium boilers by thin-film evaporation at a temperature of from 180° C. to 250° C. and a pressure of from 0.1 mbar to 20 mbar.

22. The process of claim 19, wherein the vapors of stage c) are fed, after further distillative purification, into reaction stage a).

23. The process of claim 2, wherein the separation in stage d) is carried out at a temperature of from 180 to 260° C., and under a pressure of from 0.01 to 10 mbar.

24. The process of claim 2, wherein stage d), if employed, is carried out with the aid of a thin-film or short-path evaporator.

25. The process of claim 2, wherein by-products from stage d) are discharged and discarded.

26. The process of claim 2, wherein the stream in stage c), before it is recycled into stage d), is processed in such a way that it is divided before its distillative purification into two substreams of which one substream is fed directly to the deblocking reaction.

27. The process of claim 2, wherein the stage e) is carried out in a combined cleavage and rectification column.

28. The process of claim 2, wherein, in stage e), thermal cleavage is effected continuously in the presence of at least one catalyst at a temperature of from 180 to 280° C. and under a pressure of from 0.1 to 200 mbar.

29. The process of claim 2, wherein, in stage e), cleavage is effected without solvent in a liquid phase.

30. The process of claim 2, wherein stage e) is carried out in the presence of at least one catalyst.

31. The process of claim 2, wherein the thermally induced diurethane cleavage of stage e) is carried out in a tubular furnace or an evaporator selected from the group consisting of falling-film, thin-film, bulk evaporators and combinations thereof.

32. The process of claim 2, wherein, in stage e), the conversion of diurethane to diisocyanate is within the range of from 10 to 95% by weight, based on the weight of the diurethane feed.

33. The process of claim 2, wherein, in stage e), a portion of the reaction mixture which comprises unconverted diurethanes, high-boiling by-products and other reutilizable and nonutilizable by-products is continuously discharged.

34. The process of claim 33, wherein the amount of the discharge is from 10 to 60% by weight, based on the weight of the feed.

35. The process of claim 2, wherein stage f) is carried out in a combined cleavage and rectification column.

36. The process of claim 2, wherein operation is effected at a temperature of from 95 to 260° C., and a pressure of from 0.5 to 250 mbar.

37. The process of claim 2, wherein, in stage g), the crude fraction obtained from stage f), consisting of cycloaliphatic diisocyanate, partially cleaved cycloaliphatic diurethane and optionally a small fraction of cycloaliphatic diurethane, is purified by distillation at a temperature of from 95 to 260° C., and under a pressure of from 0.5 to 150 mbar.

38. The process of claim 2, wherein the fraction obtained in stage g) is isolated as a pure product or recycled into stage i).

39. The process of claim 2, wherein, in stage h), operation is effected at a temperature of from 180 to 270° C., and under a pressure of from 0.01 to 100 mbar.

40. The process of claim 2, wherein stage h) is effected by extraction.

41. The process of claim 2, wherein, in stage h), the bottoms discharge is divided before its distillative purification into two substreams of which one is fed directly to the reurethanization stage i).

42. The process of claim 41, wherein the two substreams are divided in a ratio of from 99:1 to 1:99.

43. The process of claim 2, wherein stage i) is carried out in a continuous tank battery or in a tubular reactor.

44. The process of claim 1, wherein the reaction in stage i) is effected in the presence of at least one catalyst selected from the group consisting of the group of tin carboxylate, zinc carboxylate, copper carboxylate, tin halide, zinc halide, copper halide, tertiary amines and mixtures thereof.

45. The process of claim 2, wherein, in stage j), the recycling is effected into the deblocking stage e) or into the urethanization stage i).

46. The process of claim 2, wherein, in stage j), the amount of the discharge is from 0.1 to 50% by weight based on the weight of the feed of crude polyisocyanate into the purifying distillation stage.

47. The process of claim 1 or 2, wherein said cycloaliphatic diisocyanate is a member selected form the group consisting of 1,4-diisocyanatocyclohexane, 4,4'-dicyclohexylmethane diisocyanate, 2,2'-dicyclohexylmethane diisocyanate, 2,4'-dicyclohexylmethane diisocyanate and mixtures thereof.

48. The process of claim 1 or 2, wherein said diamines are selected from the group consisting of 1,3-diaminomethylcyclohexane, 1,4-diaminomethylcyclohexane, hexane-1,6-diamine, 2,2,4-trimethylhexan-1,6-amine, 2,4,4-trimethylhexan-1,6-amine, 3-aminomethyl-3,5,5-trimethylcyclohexylamine and mixtures thereof.

49. A multistage process for continuously preparing a cycloaliphatic diisocyanate, comprising:
a) reacting at least one cycloaliphatic diamine of the formula (II)

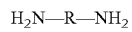

wherein R is a bivalent cycloaliphatic hydrocarbon radical having from 4 to 18 carbon atoms, the two nitrogen atoms being bonded directly to at least one hydrocarbon cycle and at least 3 carbon atoms being disposed between them, with urea and in the presence of at least one alcohol of the formula (III)

wherein $R^1$ is a radical as remains after removal of the hydroxyl group from a primary or secondary (cyclo) aliphatic alcohol having from 3 to 8 carbon atoms, in the absence or presence of a catalyst, to give at least one crude cycloalkylenebisurea of the formula (IV)

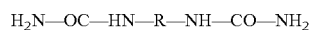

wherein R is a divalent cycloaliphatic hydrocarbon radical having from 4 to 18 carbon atoms,
with the proviso that the two nitrogen atoms flanking the two Rs are bonded directly to a hydrocarbon cycle and at least 3 carbon atoms are disposed between them, and
simultaneously continuously removing the formed ammonia;
wherein said reacting is in a distillation reactor at a temperature of from 100 to 145° C. and a pressure of from 0.7 to 1.8 bar;
wherein the reactants are introduced in a molar diamine: urea:alcohol ratio of 1:2.0 to 2.4:3 to 10 continuously to an uppermost tray of said distillation reactor and the ammonia released is driven out by alcohol vapors which are introduced in a bottom of the distillation reactor;
wherein the amount of alcohol introduced in the bottom to drive out the ammonia is from 0.05 to 3 kg/kg of bisurea; and
the amount of alcohol thus introduced is drawn off at the top together with the ammonia formed, freed of residual ammonia after partial condensation in an alcohol recovery column, and recycled into the bottom;
b) converting said crude cycloalkylenebisurea in a second reactor using said alcohol of the formula (III) used in a) as a solvent while continuously driving off the released ammonia to give cycloalkylenediurethane of the formula (V)

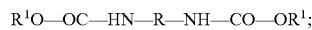

wherein R is as defined in formula (IV) and $R^1$ is as defined in formula (III), to obtain a reaction mixture containing said alcohol, a dialkyl carbonate and/or alkyl carbamate;
c) removing the alcohol, the dialkyl carbonates and/or alkyl carbamates from said resulting reaction mixture, and
recycling said alcohol into the reaction stage a);
d) fully or partially dispensing with a removal of any high-boiling residue present in said reaction mixture;
e) continuously and thermally cleaving the reaction mixture comprising the diurethane purified by steps c) and d) without solvent in the presence of a catalyst, at a temperature of from 180 to 280° C., and under a pressure of from 0.1 to 200 mbar, in such a way that a portion of from 10 to 60% by weight of the reaction mixture, based on the feed, is constantly discharged; thereby obtaining at least one cleavage product;
f) separating the cleavage product by rectification into crude cycloaliphatic diisocyanate and alcohol;
g) purifying the crude cycloaliphatic diisocyanate by distillation, to obtain a purified product fraction which is isolated;

h) separating a bottoms discharge from e) into a material-of-value stream and a waste stream, and discharging the waste stream which is rich in high boiler components from the process and disposing thereof;

i) reacting the material-of-value stream from h) with the alcohol from f) in the presence or absence of a catalyst within from 1 to 150 mm, at a temperature of from 20 to 200° C., and a pressure of from 0.5 to 20 bar, and the molar ratio of NCO groups of the material-of-value stream to OH groups in the alcohol is up to 1:100;

j) continuously discharging a portion of the bottoms fraction of the purification by distillation g) and conducting said portion into the cleavage reaction e) and/or into the urethanization stage i);

k) optionally, recycling the top fraction obtained in the purification by distillation of the crude cycloaliphatic diisocyanate into the urethanization stage i); and l) recycling the reurethanized stream from i) into stage b) and/or c);

thereby obtaining a cycloaliphatic diisocyanate of the formula (I)

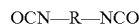

OCN—R—NCO wherein R is a bivalent cycloaliphatic hydrocarbon radical having from 4 to 18 carbon atoms, with the proviso that the two isocyanate groups are bonded directly to a hydrocarbon cycle and at least 3 carbon atoms are disposed between the two isocyanate groups.

* * * * *